United States Patent [19]

Volinsky

[11] Patent Number: 5,342,379
[45] Date of Patent: Aug. 30, 1994

[54] SAFETY SCALPEL

[76] Inventor: Fredric G. Volinsky, 11 Church St., Apt. 514, Salem, Mass. 01970

[21] Appl. No.: 69,526

[22] Filed: Jun. 1, 1993

[51] Int. Cl.$^5$ .............................................. A61B 17/32
[52] U.S. Cl. .................................... 606/167; 30/162; 30/335
[58] Field of Search .............. 606/167, 172, 180, 170; 30/340, 337, 162, 335

[56] References Cited

U.S. PATENT DOCUMENTS

| | | | |
|---|---|---|---|
| 4,444,184 | 4/1984 | Oretorp. | |
| 4,491,132 | 1/1985 | Aikins | 606/167 X |
| 4,499,898 | 2/1985 | Knepshield et al. | 606/167 X |
| 4,735,202 | 4/1988 | Williams | 606/167 |
| 4,985,035 | 1/1991 | Torre | 606/167 |

FOREIGN PATENT DOCUMENTS

| | | | |
|---|---|---|---|
| 3722899 | 1/1989 | Fed. Rep. of Germany | 606/167 |
| 2113550 | 8/1983 | United Kingdom | 606/167 |

*Primary Examiner*—Michael H. Thaler
*Attorney, Agent, or Firm*—Samuels, Gauthier & Stevens

[57] ABSTRACT

A safety scalpel which comprises a disposable cartridge and a permanent handle. The disposable cartridge is releasably engaged to the handle. The scalpel is received solely within the cartridge and can be extended and retracted as desired. The biased retraction of the scalpel minimizes injury to operating personnel. The disposable cartridge enhances safety procedures.

2 Claims, 1 Drawing Sheet

SAFETY SCALPEL

BACKGROUND AND BRIEF SUMMARY OF THE INVENTION

With the present AIDS epidemic and Hepatitis B and C epidemics, accidental needle sticks and scalpel cuts have become of much more concern to health-care personnel. The conversion rate for HIV positive needle sticks is 1 in 250 sticks. The conversion rate for scalpel cuts is unknown but according to a study of 10,000 health care workers, it is believed that the conversion rate is higher. The personal risk to the health care worker and the cost to society of a disabled and dying health care worker because of an accidental cut, supports there is a personal and a monetary incentive to improve scalpel technology and safety. The scalpel has not had many basic changes made in the past 100 years other than disposable blades and micro-surgical sizes.

Most cuts occur in specific situations, the most common is the passing of a used scalpel to a scrub nurse. Another is when a surgeon swabs a bleeder and accidently stabs himself (when he forgets that the scalpel is in his other hand). Residents are also at risk when they assist a surgeon and their hands are in the surgical field. Trauma cases are another high risk situation in which an accidental laceration can occur because there many people simultaneously working on these cases and people are rushing to perform their tasks. Most accidental cuts do not occur when the surgeon is actually trying to cut tissue. If the scalpel could be automatically disarmed when not cutting then a majority of accidental scalpel cuts could be avoided.

Safety scalpels are known that have a retractable external sheath but they require two hands to operate and are not automatic.

The present invention in its broadest aspect embodies a retractable blade scalpel assembly wherein the blade is retracted by simply using a digit of the hand holding the scalpel to actuate a release mechanism. The blade retracts into the handle with a shift of the thumb or the index finger, depending upon which side of the scalpel the release mechanism is located. This retraction can be affected after each cut has been made. The retraction is a single hand operation with out any risk of cutting oneself.

The invention in a preformed embodiment comprises a disposable cartridge secured to a permanent scalpel handle. The retractable blade is received in the cartridge. The handle is auto clavable and weighted for balance. The disposable cassette is ergonomically designed in different sizes for different blade sizes. The cartridges can be recycled in special bins to reduce cost and decrease medical waste.

DESCRIPTION OF THE PREFERRED EMBODIMENT(S)

Figure 1:
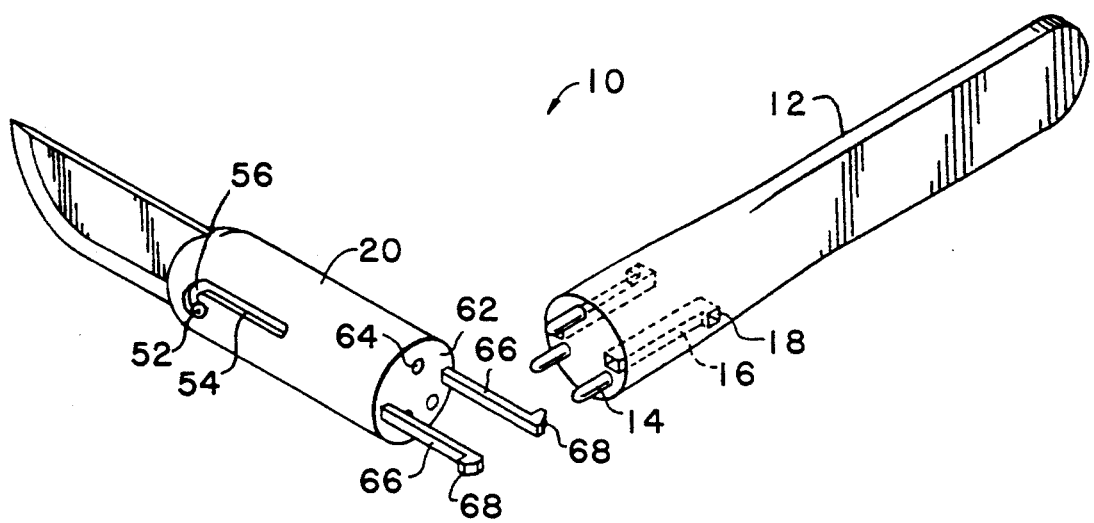
FIG. 1 is an exploded perspective view of a safety scalpel embodying the invention.

A safety scalpel embodying the invention is shown generally at 10 and comprises a permanent handle 12. The handle 12 is characterized by three locator pins 14 arrayed circumferentially and equally on the facing surface of the handle and extending outwardly therefrom.

Each side of the handle 12 is characterized by a guide track 16 which extends from the facing surface of the handle rearwardly. The guide tracks 16 terminate in locking apertures 18 which are formed in the surface of the handle 12.

A disposable cartridge is shown generally at 20 and comprises an elongated slot 22 the slot having longitudinal edges 24 and 26. The slot 22 is characterized by a rear wall 28.

A scalpel 40 comprises a blade 42 joined to a shank 44. Where the shank joins the blade are shoulders 46 and 48. The scalpel 40 is slidably received in the slot 22. When the scalpel is in its retracted position, the rear surface of the shank 44 butts the rear wall 28 to limit the movement of the scalpel 40. When the scalpel 40 is in its retracted position, the scalpel 40 is fully received within the cartridge. On one side of the blade is secured a flexible knob 52. The cartridge 20 has formed on one side an elongated track 54 having a U-shaped recess 56 at one end thereof. Springs 60 are received in the edges 24 and 26. One end of each spring is fastened, such as adhesively, to the rear wall 28, and the other end of the spring is fastened, such as adhesively, to the shoulders 46 and 48. The springs 60 bias the scalpel 40 to its retracted position.

The cartridge 20 further comprises a rear surface 62 having locator holes 64. Locking members 66 extend from the rear surface 62 of the cartridge 20. The members 66 are characterized by locking pins 68.

The slot 22, scalpel 40, edges 24 and 26 and springs 60 are dimensioned such that the scalpel 40 may freely reciprocate along a longitudinal axis coincident with the longitudinal axis of the scalpel but without movement either along or about any other axis. That is, the scalpel has a single degree of freedom in translation along its longitudinal axis. The slot 22 is essentially rectangular in cross section when viewed from the end of the cartridge 22.

Figure 2:
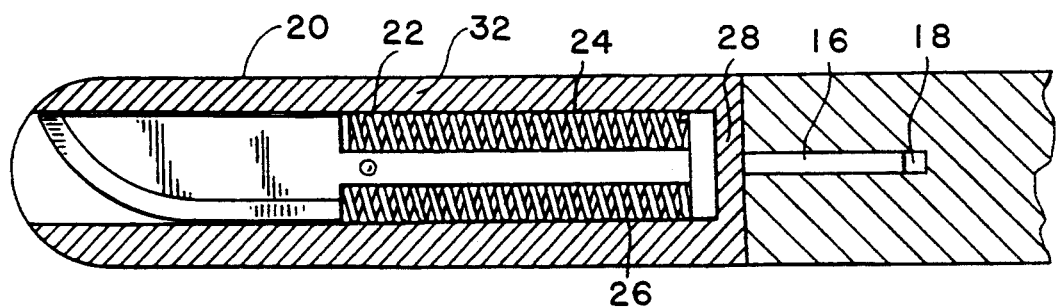
FIG. 2 is a side view of a disposable retractable cartridge assembly.
Figure 3:
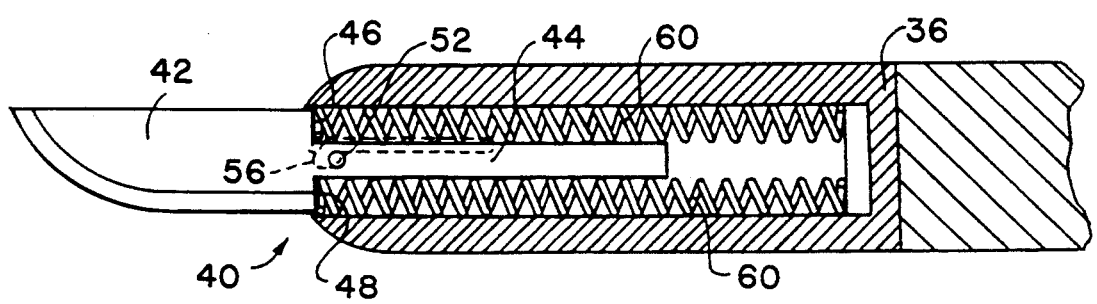
FIG. 3 is a further side view of the cartridge assembly.

In the operation of the invention, the scalpel 40 is received in the slot 22. The scalpel moves between an extended position shown in FIG. 3 and a retracted position shown in FIG. 2. The springs 60 bias the blade 42 of the scalpel 40 inwardly to its retracted position.

The cartridge 20 is secured to the handle 12 by aligning the locator pins 14 with the corresponding locator holes 64 in the rear surface 62 of the cartridge assembly. The locking members 66 slide along the guide tracks 16 and the pins 68 engage the locking apertures 18. These members 66 are biased outwardly.

After the cartridge has been secured to the permanent handle 12 and the knife is to be used for cutting the knob 52 is moved forwardly, together with the scalpel 40, in the elongated track 54. When the flexible knob 52 is in registration with the recess 56, the knob 52 is directed downwardly and into the recess 56. The springs 60 draw the knob into the recess 52 to lock the scalpel 40 into its extended position. When the scalpel 40 is not being used the knob 52 is moved forwardly and upwardly from the recess 56 and the springs 60 drive the blade to its retracted position.

The preferred invention has been described in reference to a permanent handle and a disposable cartridge with certain structures to effect securing the cartridge to the handle and to lock the scalpel in its extended position. Other mechanisms which are the functional equivalent of the mechanisms described in the preferred embodiment of the invention will be apparent to those skilled in the art. For example, a cartridge could be secured to the handle through threading the cartridge to the handle, the cartridge could snap into the handle, such as a socket that snaps into a wrench handle, etc. The locking mechanism could comprise a depressible button secured to the scalpel, which button would be depressed, the scalpel extended and the button released, locking the scalpel in position.

In an alternative embodiment, if the cartridge is not desired, the handle 12 and cartridge 40 can be formed integrally, eliminating the pins 14, tracks 16, apertures 18, holes 64 and members 66.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A safety scalpel assembly which comprises:

a handle which includes a facing surface, the facing surface of the handle characterized by locating pins and further characterized by guide tracks, which guide tracks terminate in locking apertures;

a cartridge having an elongated slot formed therein, a rear wall formed in the cartridge and aligned with the slot to limit the movement of a scalpel slidably received in the slot, the scalpel having a blade and a shank, said movement being solely within the cartridge, the scalpel adapted to be fully recessed in the cartridge when the scalpel is in a retracted position and to extend from the cartridge when the scalpel is in an extended position, a track formed in the wall of the housing, means to bias the scalpel to its retracted position within the slot, means to move the scalpel from its retracted position to its extended position, said means to move secured to the scalpel and extending into he track and travelling along the track, means to lock the scalpel in its extended position; and the cartridge having a facing surface, which abutts to the facing surface of the handle and wherein the facing surface of the cartridge is characterized by locator holes and locking members, the pins of the handle received in the holes and the locking members releasably engaged in the locking apertures of the handle when the handle is secured to the cartridge.

2. The assembly of claim 1 wherein the means to lock the scalpel in its extended position comprises a locking recess formed in the track and the means to move the scalpel is configured to engage the locking recess.

* * * * *